United States Patent
Widgerow

(10) Patent No.: US 8,071,139 B2
(45) Date of Patent: Dec. 6, 2011

(54) TREATMENT OF DAMAGED SKIN

(76) Inventor: Alan David Widgerow, Gauteng (ZA)

( * ) Notice: Subject to any disclaimer, the term of this patent is extended or adjusted under 35 U.S.C. 154(b) by 166 days.

(21) Appl. No.: 12/554,364

(22) Filed: Sep. 4, 2009

(65) Prior Publication Data

US 2010/0062085 A1     Mar. 11, 2010

Related U.S. Application Data

(60) Provisional application No. 61/094,170, filed on Sep. 4, 2008.

(30) Foreign Application Priority Data

Sep. 18, 2008 (ZA) ................ 2008/08004
Jun. 8, 2009 (ZA) ................ 2009/04000

(51) Int. Cl.
*A01N 65/00* (2009.01)
(52) U.S. Cl. ...................................... 424/725
(58) Field of Classification Search ............ None
See application file for complete search history.

(56) References Cited

U.S. PATENT DOCUMENTS

| | | | |
|---|---|---|---|
| 4,707,360 | A | 11/1987 | Brasey |
| 5,368,553 | A | 11/1994 | Newman |
| 5,833,998 | A | 11/1998 | Biederman et al. |
| 6,159,494 | A | 12/2000 | Widgerow et al. |
| 6,261,605 | B1 | 7/2001 | Singh-Verma |
| 6,280,765 | B1 | 8/2001 | Gueret |
| 6,437,004 | B1 | 8/2002 | Perricone |
| 6,743,449 | B2 | 6/2004 | Pinnell et al. |
| 7,160,560 | B2 | 1/2007 | Pinnell |
| 7,344,737 | B2 | 3/2008 | Pushpangadan et al. |
| 7,402,669 | B2 | 7/2008 | Loiseau et al. |
| 2008/0118581 | A1 | 5/2008 | Loiseau et al. |
| 2008/0226700 | A1 | 9/2008 | Cozzolino |
| 2009/0117061 | A1 | 5/2009 | Gross |
| 2010/0303872 | A1 | 12/2010 | Dumas et al. |

FOREIGN PATENT DOCUMENTS

| | | |
|---|---|---|
| ZA | 1997/10848 | 12/1997 |
| ZA | 2008/02517 | 3/2008 |
| ZA | 2008/08004 | 9/2008 |
| ZA | 2009/04000 | 6/2009 |
| ZA | 2010/05770 | 8/2010 |

OTHER PUBLICATIONS

Dhar, A. et al. Synthesis, Structure-Activity Relationships, and RARy-Ligand Interactions of Nitrogen Heteroarotinoids. J. Med. Chem., 1999, 42, pp. 3602-3614.
Gelse K. et al. Collagens structure, function and biosynthesis. Advanced Drug Delivery Reviews 55 (2003) 1531-1546.
Mustoe, T.A. et al. International Advisory Panel on Scar Management. International clinical recommendations on scar management. Plast Reconst Surg, 2002, 110(2):560-571 (review) Aesth Plast Surg.
Shah, M. et al. Neutralising antibody to TGF-beta 1, 2 reduces cutaneous scarring in adult rodents. J Cell Sci, 1994, 107(5):1137-1157.
Soyun Cho et al. Phosphatidylserine prevents UV-induced decrease of type I procollagen and increase of MMP-1 in dermal fibroblasts and human skin in vivo; Journal of Lipid Research vol. 49, 2008.
Widgerow, A.D. et al. New Innovations in scar management. Aesthetic Plast Surg 2000, 24(3):227-334.
Widgerow AD. Scar management—marrying the practical with the science. Would Healing Southern Africa 2010; 3(1):7-10.
Wilgus, T.A. et al. Reduction of scar formation in full-thickness wounds with topical celecoxib treatment. Wound Repair Regen, 2003, 11(1):25-34.

*Primary Examiner* — Michael Meller
(74) *Attorney, Agent, or Firm* — Knobbe, Martens, Olson & Bear, LLP

(57) ABSTRACT

A medicament for treating skin is described. It comprises essentially of *bulbine frutescens, centella asiatica* and a phenol derived from olive oil preferably oleuropein. The medicament may be used in the treatment of scars formed during surgery. It may also be used cosmeceutically in the treatment of aged skin where it may be used with phosphatidylserine. The medicament can also act in conjunction with anti-acne treatment to diminish scarring from the acne condition.

19 Claims, No Drawings

TREATMENT OF DAMAGED SKIN

CROSS REFERENCE TO RELATED APPLICATIONS

This application claims priority from U.S. patent application Ser. No. 61/094,170 filed Sep. 4, 2008 and from South African Patent Applications Nos. 2008/08004 and 2009/04000 filed respectively on Sep. 18, 2008 and Jun. 8, 2009.

BACKGROUND OF THE INVENTION

This invention relates to the treatment of skin especially damaged skin. The invention is concerned with skin that is damaged as a result of scarring consequent upon surgery and as a result of ageing or damage by excessive exposure to ultra violet light. The invention is also concerned with the treatment of skin for cosmeceutical purposes.

In U.S. Pat. No. 6,159,494 (Widgerow and Chait) (the contents whereof are incorporated by this reference) there is described a method of treatment of damaged human skin. The treatment consists of applying to the skin medicament for topical application such as an ointment comprising as the active ingredients *bulbine frutescens* and *Centella asiatica*. Where this medication is used for the treatment of scarring it is used in conjunction with a tape which is applied to the skin about the scar to prevent or minimise any tension that is applied to the scar.

*Bulbine frutescens* is a common garden plant that grows in South Africa. I have now found that *bulbine frutescens* has important hydrating properties. In addition the extracts (peptides) of *bulbine frutescens* have decorin-like effects on wound healing. It appears that these polypeptides mimic the effect of decorin and rearrange collagen in a uniform manner during the process of fibrillogenesis and collagen regeneration. This provides an important adjuvant to the *Centella asiatica* extract in modulating, uniformly arranging, and maturing collagen during the process of healing.

I have found too that extra constituents provide for a multimodality approach to scar management covering all phases of the wound healing cascade. One of the most important physiologic responses to wounding is that of inflammation. It can also be one of the most destructive: over exuberant inflammation is thought to be cause of most chronic arthritic conditions, heart disease, and chronic wound pathogenesis. Along the physiologic path to scar formation, excess inflammation will result in an exaggerated scar. Suture materials are frequently and unavoidably associated with this phenomenon. On the other hand, controlled inflammation speeds up the process of scar maturation with minimal fibrosis.

Phenols (oleuropein) extracted from olive oil have known anti-inflammatory and antibacterial properties. I have found that when used at low doses in combination with *bulbine frutescens* and *Centella Asiatica* helpful inflammation is unaffected, whereas exuberant inflammation, typical of foreign body reactions, can be down regulated or modulated.

SUMMARY OF THE INVENTION

Thus according to one aspect of the invention there is provided a medicament, such as a gel, cream, ointment or the like for topical application to the skin comprising *bulbine frutescens* and *Centella asiatica* supplemented by one or more phenols extracted from olive oil preferably comprising oleuropein. Preferably the phenols comprise about 0.18% to 0.3% mass/volume of the medicament when used for the treatment of damaged skin such as skin cut in an operation and about 0.018% to 0.03% when the medicament is used for cosmetic purposes. The *Centella asiatica* may comprise from about 0.45% to 0.55% and preferably about 0.5% mass/mass of the medicament. The *Bulbine Frutescens* may comprise 9.9% to 11.0% m/m of the medicament. The medicament preferably further comprises silicone conveniently in the form of dimethicone.

I have also found in addition that silicone, either in the form of sheeting or various topical applications which include dimethicone when used in conjunction with *bulbine frutescens* and *Centella Asiatica* provides an important complement to the action of *bulbine frutescens* as an hydrating agent.

I have further found that efforts at controlling scar outcome (including keloid scar formation) should be initiated at the time of wounding when the trigger for the sequence of healing begins or as soon thereafter as possible. According to a further aspect of the invention there is provided a method of treating a scar comprising applying a medicament as set out above to the scar at the time of provisional scar matrix formation, the effect on subsequent matrix dissolution, maturation, whereby the scar formation is tackled more efficiently. Preferably the treatment of the scar is commenced immediately following wound closure at the time of surgery or within a day or two thereafter.

According to another aspect of the invention there is provided a method of treating damaged skin including applying a medication as set out above to the skin. Where the skin is caused by a wound cut during an operation, preferably a tape is applied to the length of the scar and the gel is applied to the tape. The application of the tape and gel is commenced as soon as convenient after the wound has been formed.

Embodiments of the invention will now be described by way of example with reference to the following examples.

EXAMPLE 1

Sixty patients each having a scar following simple skin excisions formed part of this example. Thirty of the patients had their scars treated; thirty had their scars untreated (10 face, 10 limbs, 10 back in each group).

The treated patients were each treated as will be described with a scar gel of the invention. The scar gel comprised the ingredients and percentages as set out in TABLE I.

The scar gel comprised (an in further reference to "the scar gel" is meant the gel set out in this table).

TABLE I

| Ingredient | Description or action |
| --- | --- |
| Aqua dest | Distilled water |
| poloxamer | Gel Matrix |
| glycerol-polyethylene glycol oxystearate | Surfactant. helps in collecting oil droplets into aqueous gel matrix |
| Propylene glycol | Solvent |
| dimethicone | Oil carrier Silicone |
| oleuropein (olive leaf extract) | Antiseptic properties (anti-fungal; anti bacterial and anti inflammatory |
| Triterpenic fraction of *Centella asiatica* | Reducer of Scar tissue This converts collagen III to collagen I |
| phenoxyethanol | Preservative against fungi |
| Methylhydroxy-benzoate | Preservative against germs |
| lactic acid | To bring acidity of the product to near skin pH which is lower than 5.5 |
| *Bulbine Frutescens* | For re-arranging collagen fibrils. |
| Microporous tape | |

The triterpenic fraction of *Centella asiatica* comprises 0.5% m/m of the medicament; the *Bulbine Frutescens* comprises 10.0% m/m of the medicament; and the oleuropein comprises 0.18% to 0.3 mass/volume of the medicament.

Patients were randomized to receive either routine postoperative care with tape alone (bilateral cosmetic cases) (i.e. the untreated patients) or combined tape with topical scar gel or no treatment (routine for small skin excisions) (i.e. the treated patients). Where one side was treated, the side selected for treatment was also randomized (at the end of surgery, the nursing staff drew lots to choose the right or left side for treatment). All scars were assessed and photographed at follow-up at 1, 2, and 6 months following surgery.

In contrast to known management programs, scar management was initiated in the treated patients immediately following surgery.

For small local excisions of skin tumours, the wounds were left without a dressing on the face and gel was applied directly to the site and continued twice daily by the patient as long as desired and normally for the full six month period.

Scar Assessment

In an effort to combine all recent recommendations for scar assessment, elements of different scales were incorporated into the assessment parameters. Thus, elements of the Vancouver Scar Scale were incorporated into the scale of morphologic features. Patient and observer assessment charts were also included in the assessments as previously recommended.

Data Analysis

The data were revised into a format compatible with the statistical program using SAS v9. Differences between treated and untreated patients were determined using the Kruskal/Wallis test with 0.05 considered significant.

Results

Scar Morphology

In the patients there were no significant differences apparent one month after the operation, the scars were significantly improved after two months in the treated versus the untreated group. Over the six months the morphologic grading scores improved only in treated but not untreated patients.

Scar thickness and regularity of the treated scars were rated as being significantly better than untreated scars, with scar stiffness reaching borderline significance.

Visual Examination

Observers rated scar vascularization, pigmentation, thickness, relief, and pliability of the scar. All these parameters were significantly improved (p\0.005) in treated patients compared with the parameters of untreated patients.

Observers noted scar hypopigmentation, hyperpigmentation, and mixed (hypo/hyperpigmentation) scars in 16 of the treated patients (89%). This compared favourably (p=0.04) with the untreated patients in whom 14/23 (61%), 4/23, and 5/23 had hypo-, hyper-, and mixed pigmentation (hypo/hyperpigmentation) scars respectively.

EXAMPLE II

Twenty patients each patient with two excisions formed part of this study. Of the two excisions of each patient, one was treated and one untreated (10 back, 5 face, 5 limbs).

On the back and limbs the site was covered with macroporous tape. Scar gel was applied immediately following surgery on to the surface of the tape, saturating it and producing an occlusive type of dressing. Patients were instructed to apply scar gel to the surface of the tape twice a day morning and night.

The scar assessment was as indicated above.

In patients with two excisions where one was treated and the other not (Group 1) the differences in scar morphology became significantly apparent at 6 months. As with Example 1, the treated but not the untreated scars showed significant improvement over the 6 months.

Visual Examination

Observers rated scar vascularization, pigmentation, thickness, relief, and pliability of the scar. Except for the vascularization rating, all other parameters were significantly improved.

EXAMPLE III

Ten patients undergoing skin surgery were treated with the scar gel as set out in Table 1. The ten patients had 20 scars following bilateral breast surgery, one side treated with tape alone, one side treated with tape and gel (5 breast augmentations, 5 breast reductions).

In patients to whom the gel was applied, the scar gel was applied liberally to the area prior to application of the dressing. The gel was not massaged in but was left on the surface to ensure a reasonable amount of gel on the scar surface while the dressing was left undisturbed for seven to ten days.

In cases where the dressing was changed the following day (breast reduction procedures), scar gel was reapplied to the selected side. Following the dressing change after seven to ten days, patients continued with the program for three to six months until the scar was considered mature (nonsymptomatic, white).

The scar assessment was as indicated above.

Similar results were found for this group of breast augmentation and reduction patients. Treated scars showed significant morphologic improvement after two months with borderline significance at 1 and 6 months compared to the untreated scars (i.e. the scars treated by tape alone).

Only treated scars showed significant improvement in itchiness, with scar stiffness, thickness, and regularity approaching significance.

Visual Examination

Observers rated scar vascularization, pigmentation, thickness, relief, and pliability of the scar. Vascularization and pigmentation were improved in treated scars with scar thickness, relief, and pliability reaching borderline significance.

EXAMPLE IV

Thirty patients with varying cosmetic procedures with 50 scars all treated and compared with historical outcomes for hypertrophic scarring (10 breast augmentations, 10 breast reductions, 10 abdominoplasties). The scars were treated immediately after surgery with the scar gel mentioned in table 1.

The scar assessment was as indicated above.

The results showed that these patients who underwent a variety of procedures and showed improvement in scar morphology over the 6 months of follow-up. Overall morphology improved in all the groups.

Visual Examination

Observers rated scar vascularization, pigmentation, thickness, relief, and pliability of the scar. All these parameters were significantly improved (p\0.005) in treated patients compared with the parameters of untreated patients.

Observers noted scar hyperpigmentation were similar in the treated patients in Example I.

GENERAL

It will be seen therefore that in the important areas of scar assessment, the patients treated in all examples showed statistically significant improvement in all parameters. Morphologic features together with stiffness, thickness, and irregularity in POSA and thickness and relief in OSA are probably the most important parameters for analysing scar hypertrophy.

A number of patients had undergone previous surgery. The first scars (i.e. from the previous surgery) were compared with those produced by the new surgical procedure where the scar program was used. In two of these cases previous infra-mammary scars were excised in patients who had undergone reduction surgery elsewhere. The new infra-mammary scars demonstrated superior scar outcomes to those of the previous mid-line and periareolar scars.

Morphologic assessment of scars at two months (not one month) were usually (although not always) reasonable predictors of long-term scar outcome. Predictors of poor outcome of long-term results appeared to be that of early signs of scar thickening or hypertrophy (Grade 3 morphologic scale).

It is well accepted that ongoing inflammation retards wound healing. This is especially important in chronic non-healing wounds where proteases and reactive oxygen metabolites are responsible for much on the ongoing damage, antiproliferative effects, and non-healing seen in these wounds. The negative effects of exuberant inflammation are not limited to chronic wounds: in acute wounds low-grade ongoing inflammation results in increased cytosine elaboration (especially TGFb1 and 2) and a profibrotic state with a resultant exaggerated scar. This inflammation can be initiated by tension on the scar, foreign material (long-standing sub-cuticular sutures), bacteria, biofilm, and many other scenarios. Thus, control of inflammation during the healing phase is a desired goal. Newly pressed extra-virgin olive oil contains phenolic compounds (oleocanthal, oleuropein) that act as a natural anti-inflammatory compound that has a potency and profile strikingly similar to that of Ibuprofen. Although structurally dissimilar, both these molecules inhibit the same cyclo-oxygenase enzymes in the prostaglandin-biosynthesis pathway. This anti-inflammatory effect has important implications for scar control.

Surface Hydration

Dimethicone has been added to the mix as an extremely efficient hydrating agent complementing the action of *Bulbine frutescens*. An additional consideration in this new formulation was to manufacture a product with a short-term "sticky" consistency that works synergistically with the tape. This has been successfully achieved; the tape saturated with the gel adheres to the wound more effectively than previous formulations. Additionally the mixture heals with the formation of a barrier film which protects the scar from environmental influences and ensures a certain amount of support to the scar.

In Example III (comparing gel and tape with tape alone), patients repeatedly observed that the tape and gel combination had far superior adhesive qualities and needed to be changed much less frequently. A comprehensive efficient occlusive dressing is thus achieved. In situations where tape was not used, this stickiness did not last long and no patient complained of any problem or unpleasantness with its application. Thus, support, hydration, collagen maturation, and balanced inflammation are areas targeted in this multimodality regime. We believe that the tape/cream combination represents an interactive occlusive dressing that positively effects scar outcome.

Timing

Early scar control starting at the time of wounding is new in the improvement of scar outcome. Thus although the application of the scar gel can be commenced from seven to fourteen days after surgery preferably the scar gel is applied at the time of initial dressing at the end of the surgical procedure or the following day after surgery and as an immediate and continued application to the wound for small local excisions of skin lesions was applied in all the Examples. This resulted in the best scar results I have seen to date as it impacts positively on the appearance of the scar. This was particularly evident in the patients mentioned in Example III where those treated immediately with tape and scar gel had better outcomes in all parameters measured.

Support by microporous tape may not always be critical to the process in cases where the wound is supported by subcuticular sutures; this is not the case in smaller excisions of skin lesions, where tension on the skin is expected to be much less in these cases. Thus, microporous tape use was halted following 6 weeks of use. Hydration, controlled inflammation, and collagen maturation are all expected to be advantageous. I am not too concerned about identifying one particular dominant modality because I believe the secret of success lies in the very nature of multimodality synergy. The agents all acting in unison, converting the microporous tape to an occlusive interactive dressing, is likely to be the mechanism of action of this treatment. However, I do believe that the choice of agents, with their individual different effects, is far more beneficial than a simple hydrating agent. Reactivity and redness of wounds were markedly decreased in the treated cases; this was likely the positive effect of diminished inflammation, with its ultimate beneficial effect on scar outcome.

The invention is not limited to the precise description set out above. The carrier for the active ingredients may be an ointment or a cream. The non-active ingredients may be varied as desired as may the proportions of such ingredients. The proportions of the active ingredients may be varied as follows. The amount of *centella asiatica* can be reduced to between 0.1% and 0.25% of the medicament to produce a milder medicament where the goal is texture modification, e.g. when treating skin which may be applied with advantage as a result of ageing or damage by excessive exposure to ultra violet light.

The scar gel modified as mentioned may also be used for cosmetic purposes. The oleuropein content will be reduced by a factor of ten to 0.018 to 0.03% mass to volume of the final preparation. This modified scar gel may be used to treat aged skin. The treatment would be as follows:- each morning a collagen booster such as phosphatidylserine is applied to the skin together with an antioxidant and a sun protection cream. In the evening the collagen booster (phosphatidylserine) is applied to the skin together with the modified scar gel. Aged skin is characterised by a shortage of collagen and irregular collagen the fibrils of which are clumped or aggregated in nature. Young skin on the other hand is associated with uniform collagen fibres and good amounts of type 1 collagen. By treating the aged skin as described will (i) stimulate the formation of procollagen (because of the effect of the phosphatidylserine) and (ii) type 1 collagen (because of the *centella asiatica*) (iii) promote uniformly spaced collagen (due to the effect of the *bulbine frutescens*) (iv) mop up of free radicals that are associated with aging (due to the oleuropein and the *centella asiatica*). The combination of *centella asiatica, bulbine frutescens* and oleuropein promote an increase in collagen and its sequential modulation to a well structured form.

To the scar gel (ointment or cream) may be added other plant extracts and vitamins or provitamins for the purpose of formulating a comprehensive cosmetic skin maintenance range achieving cleansing, moisturising, healing, toning, hydrating and protecting the skin. These extracts, vitamins and provitamins include *Symphytum officinale* Provitamin B5, *Hamamelis virginiana*, *Cucumis sativus*, Zinc, *Enantia chlorantha*, German Camolmile, Retinyl palmitate, *Macrocystis pyrifera*, Prolamines, and *Imperata cylindrica*.

In the context of collagen modulation, particularly when considering anti-aging intervention, the *Centella*, *Bulbinela* and Oleuropein may be used in conjunction with phosphatidylserine. This agent stimulates the formation of procollagen, a collagen precursor. This new collagen is then acted on by the combination of *centella*, *bulbinela* and oleuropein to induce maturation of the collagen. This sequence would have important anti-aging benefits.

The scar gel in the combination referred to above may be used as an adjunct to anti-acne treatment. In this context it is used to minimise the eventual scarring resultant from the acne. It is usually used once the acute pustular phase of the acne is ending and the inflammatory phase has started. The scar gel is applied to the individual acne lesions to promote healing, decrease inflammation and improve the final outcome in terms of scarring. There may well be beneficial effects in the early pustular phases of acne due to the antibacterial and anti-inflammatory effects of oleuropein and the healing effects of *centella* and *bulbine*, but the main indication in patients with acne would be for its use in diminishing scarring.

The present invention is primarily concerned with the treatment of human subjects, but the invention may also be carried out on animal subjects, particularly mammalian subjects such as dogs, cats, livestock and horses for veterinary purposes. While subjects may be of any suitable age, the subjects are in some embodiments adult or geriatric subjects.

The term "Treat" as used herein refers to any type of treatment that imparts a benefit to an aging patient, particularly delaying or retarding the progression of the condition.

The term "Pharmaceutically acceptable" as used herein means that the compound or composition is suitable for administration to a subject to achieve the treatments described herein, without unduly deleterious side effects in light of the severity of the disease and necessity of the treatment.

The active compounds described above may be formulated for administration in a pharmaceutical carrier in accordance with known techniques. See, e.g., Remington, The Science And Practice of Pharmacy (9th Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01% or 0.5% to 95% or 99% by weight of the active compound. One or more active compounds may be incorporated in the formulations of the invention, which may be prepared by any of the well known techniques of pharmacy comprising admixing the components, optionally including one or more accessory ingredients. Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

In addition to active compound(s), the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

The following references are cited herein.

1. Widgerow A D, Chait L A, Stals R, Stals P J (2000) New innovations in scar management. Aesthetic Plast Surg 24(3):227-234
2. Meyer M, McGrouther D A (1991) A study relating wound tension to scar morphology in the presternal scar using Langers technique. Br J Plast Surg 44(4):291-294
3. Murison M, James W (2006) Preliminary evaluation of the efficacy of Dermatix silicone gel in the reduction of scar elevation and pigmentation. J Plast Reconstr Aesthet Surg 59(4):437-439
4. Atkinson J M, McKenna K T, Barnett A G, McGrath D J, Rudd M (2005) A randomized, controlled trial to determine the efficacy of paper tape in preventing hypertrophic scar formation in surgical incisions that traverse Langer's skin tension lines. Plast Reconstr Surg 116(6):1648-1656
5. Petroni A, Blasevich M, Salami M, Papini N, Montedoro G F, Galli C (1995) Inhibition of platelet aggregation and eicosanoid production by phenolic components of olive oil. Thrombosis Res 78(2):151-160
6. Sawada Y, Sone K (1992) Hydration and occlusion treatment for hypertrophic scars and keloids. Br J Plast Surg 45(8):599-603
7. Soderberg J (1982) Treatment of keloids and hypertrophic scars with adhesive zinc tape. Scand J Plast Surg 16:261
8. Chang C C, Kuo Y F, Chiu H C, Lee J L, Wong T W, Jee S H (1995) Hydration, not silicone, modulates the effects of keratinocytes on fibroblasts. J Surg Res 59(6):705-711
9. Shah M, Foreman D M, Ferguson M W (1994) Neutralising antibody to TGF-beta 1, 2 reduces cutaneous scarring in adult rodents. J Cell Sci 107(5):1137-1157
10. Atiyeh B S (2007) Nonsurgical management of hypertrophic scars: evidence-based therapies, standard practices, and emerging methods. Aesthetic Plast Surg 31(5): 468-492
11. Hertog M G, Feskens E J, Hollman P C, Katan M B, Kromhout D (1993) Dietary antioxidant flavonoids and risk of coronary heart disease: the Zupthen Elderly Study. Lancet 342(8878):1007-1011
12. Powers P S, Sarkar S, Goldgof D B, Cruse C W, Tsap L V (1999) Scar assessment: current problems and future solutions. J Burn Care Rehabil 20(1 Pt 1):54-60
13. Beauchamp G K, Keast R S, Morel D, Lin J, Pika J, Han Q, Lee C H, Smith A B, Breslin P A (2005) Phytochemistry: ibuprofenlike activity in extra-virgin olive oil. Nature 437(7055):45-46
14. de la Puerta R, Martinez Dominguez E, Ruiz Gutierrez V (2000) Effect of minor components of virgin olive oil on topical anti-inflammatory assays. Z Naturforsch [C] 55(9-10):814-819
15. Tranter H S, Tassou S C, Nychas G J (1993) The effect of the olive phenolic compound, oleuropein, on growth and enterotoxin B production by *Staphylococcus aureus*. J Appl Bacteriol 74(3):253-259
16. Mustoe T A (2008) Evolution of silicone therapy and mechanism of action in scar management. Aesthetic Plast Surg 32(1):82-92

17. Niessen F B (1997) Effectiveness of silicone sheets in the prevention of hypertrophic breast scars. Ann Plast Surg 38(5):547 (letter)
18. Reiffel R (1995) Prevention of hypertrophic scars by long term use of paper tape application. Plast Reconstr Surg 96(7):171-175
19. Signorini M, Clementoni M T (2007) Clinical evaluation of a new self-drying silicone gel in the treatment of scars: a preliminary report. Aesthetic Plast Surg 31(2):183-187
20. Baryza M J, Baryza G A (1995) The Vancouver Scar Scale: an administration tool and its interrater reliability. J Burn Care Rehabil 16(5):535-538
21. Draaijers L J, Tempelman F R, Botman Y A, Tuinebreijer W E, Middelkoop E, Kreis R W, van Zuijlen P P (2004) The patient and observer scar assessment scale: a reliable and feasible tool for scar evaluation. Plast Reconstr Surg 113(7):1960-1965
22. Puig A, Anton G M, Mangues M (2007) A new decorin-like tetrapeptide for optimal organization of collagen fibres. IFSCC Mag 10(4):309
23. Truong P T, Lee J C, Soer B, Gaul C A, Olivotto I A (2007) Reliability and validity testing of the Patient and Observer Scar Assessment Scale in evaluating linear scars after breast cancer surgery. Plast Reconstr Surg 119(2):487-494
24. Ono I, Akasaka Y, Kikuchi R, Sakemoto A, Kamiya T, Yamashita T, Jimbow K (2007) Basic fibroblast growth factor reduces scar formation in acute incisional wounds. Wound Repair Regen 15(5):617-623
25. Wilgus T A, Vodovotz Y, Vittadini E, Clubbs E, Oberyszyn T (2003) Reduction of scar formation in full-thickness wounds with topical celecoxib treatment. Wound Repair Regen 11(1):25-34
26. Chen W Y, Rogers A A (2007) Recent insights into the causes of chronic leg ulceration in venous diseases and implications on other types of chronic wounds. Wound Repair Regen 15(4):434-449
27. van Wyk B E, Van Oudtshoorn B, Gericke N (1997) Medicinal plants of South Africa. Briza Publications, Arcadia, South Africa, p 64
28. Mustoe T A, Cooter R D, Gold M H, Hobbs F D, Ramelet A A, Shakespeare P G, Stella M, Téot L, Wood F M, Ziegler U E (2002) International Advisory Panel on Scar Management. International clinical recommendations on scar management. Plast Reconstr Surg 110(2):560-571 (review) Aesth Plast Surg
29. Colowisk, Sidney, P. and Kaplan, Nathan, O. Methods in Enzymology, Vol. XVIII, Vitamins and Coenzymes, Part C. Edited by Donald B. McCormick and Lemuel D. Wright. Section XII, PP. 335.
30. Dhar, A., Liu, S., Klucik, J., Berlin, K. D., Madler, M. M., Lu, S., Ivey, R. T. Zacheis, D., Brwon, C. W., Nelson, E. C., Birchbichler, P. J., Benbrook, D. M. Synthesis, Structure-Activity Relationships, and RARy-Ligand Interactions of Nitrogen Heteroarotinoids. J. Med. Chem. 42, pp. 3602-3614 (1999).
31. Soyun Cho, Hyeon Ho Kim, Min Jung Lee, Serah Lee, Chang-Seo Park, Sang-June Nam, Jeong-Jun Han, Jin-Wook Kim, and Jin Ho Chung. Phosphatidylserine prevents UV-induced decrease of type I procollagen and increase of MMP-1 in dermal fibroblasts and human skin in vivo; Journal of Lipid Research Volume 49, 2008.
32. Gelse K, Pöschl E and Aigner T. Collagens—structure, function and biosynthesis. Advanced Drug Delivery Reviews 55 (2003) 1531-1546.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

The composition may comprise, consist of or consist essentially of: from 0.0001, 0.001, 0.01, or 0.1 percent by weight, up to 1, 2, 5 or 10 percent by weight *Bulbine frutescens* active agent and or extract;
from 0.0001, 0.001, 0.01, or 0.1 percent by weight, up to 1, 2, 5 or 10 percent by weight *Centella asiatica* active agent or extract;
from 0.0001, 0.001, 0.01, or 0.1 percent by weight, up to 1, 2, 5 or 10 percent by weight phenol extract from olive oil active agent or extract; and
from 1, 5 or 10 percent by weight, up to 90, 95 or 99 percent by weight, pharmaceutically acceptable carrier.

I claim:

1. A gel medicament for topical application to damaged skin, said medicament consisting essentially of:
    an extract of *bulbine frutescens* in an amount from about 9% to about 11% mass per mass of the medicament;
    an extract of *Centella asiatica* in an amount from about 0.1% to about 2% mass per mass of the medicament;
    a phenol extracted from a source selected from the group consisting of olive leaf and olive oil in an amount from about 0.18% to about 0.3% mass per volume of the medicament, wherein said phenol comprises oleuropein;
    dimethicone;
    water;
    propylene glycol;
    glycerol-polyethylene glycol oxystearate;
    poloxamer; and
    phenoxyethanol.

2. The medicament of claim 1, wherein the damaged skin is damaged by a wound, a scar, acne, or aging.

3. The medicament of claim 2, wherein the wound is produced during a surgical procedure.

4. The medicament of claim 1, wherein application of the medicament to said damaged skin reduces inflammation.

5. The medicament of claim 1, wherein topical application of the medicament to said damaged skin produces an occlusive dressing without the use of microporous tape.

6. The medicament of claim 1, wherein said medicament facilitates formation of a barrier that protects the damaged skin from environmental influences and provides support for said damaged skin.

7. A gel medicament for topical application to damaged skin, said medicament consisting essentially of:
    an extract of *bulbine frutescens* in an amount from about 9% to about 11.0% mass per mass of the medicament;
    an extract of *Centella asiatica* in an amount from about 0.1% to about 2% mass per mass of the medicament;
    a phenol extracted from a source selected from the group consisting of olive leaf and olive oil in an amount from about 0.18% to about 0.3% mass per volume of the medicament, wherein said phenol comprises oleuropein; and
dimethicone;
water;
propylene glycol;
glycerol-polyethylene glycol oxystearate;
poloxamer;
phenoxyethanol; and
phosphatidylserine.

8. The medicament of claim 7, wherein the damaged skin is damaged by a wound, a scar, acne, or aging.

9. The medicament of claim 8, wherein the wound is produced during a surgical procedure.

10. The medicament of claim 7, wherein application of the medicament to said damaged skin reduces inflammation.

11. The medicament of claim 7, wherein topical application of the medicament to said damaged skin produces an occlusive dressing without the use of microporous tape.

12. The medicament of claim 7, wherein said medicament facilitates formation of a barrier that protects the damaged skin from environmental influences and provides support for said damaged skin.

13. A gel medicament for topical application to damaged skin, said medicament consisting essentially of:
an extract of *bulbine frutescens* in an amount from about 9% to about 11.0% mass per mass of the medicament;
an extract of *Centella asiatica* in an amount from about 0.1% to about 2% mass per mass of the medicament;
a phenol extracted from a source selected from the group consisting of olive leaf and olive oil in an amount from about 0.18% to about 0.3% mass per volume of the medicament, wherein said phenol comprises oleuropein;
dimethicone;
water;
propylene glycol;
glycerol-polyethylene glycol oxystearate;
poloxamer;
phenoxyethanol; and
a vitamin.

14. The medicament of claim 13, wherein the damaged skin is damaged by a wound, a scar, acne, or aging.

15. The medicament of claim 13, wherein application of the medicament to said damaged skin reduces inflammation.

16. The medicament of claim 13, wherein topical application of the medicament to said damaged skin produces an occlusive dressing without the use of microporous tape.

17. The medicament of claim 13, wherein said medicament facilitates formation of a barrier that protects the damaged skin from environmental influences and provides support for said damaged skin.

18. A gel medicament for topical application to damaged skin, said medicament consisting essentially of:
an extract of *bulbine frutescens* in an amount from about 9% to about 11.0% mass per mass of the medicament;
an extract of *Centella asiatica* in an amount from about 0.1% to about 2% mass per mass of the medicament;
a phenol extracted from a source selected from the group consisting of olive leaf and olive oil in an amount from about 0.18% to about 0.3% mass per volume of the medicament, wherein said phenol comprises oleuropein;
dimethicone;
water;
propylene glycol;
glycerol-polyethylene glycol oxystearate;
poloxamer;
phenoxyethanol; and
lactic acid.

19. A gel medicament for topical application to damaged skin, said medicament consisting essentially of:
an extract of *bulbine frutescens* in an amount from about 9% to about 11.0% mass per mass of the medicament;
an extract of *Centella asiatica* in an amount from about 0.1% to about 2% mass per mass of the medicament;
a phenol extracted from a source selected from the group consisting of olive leaf and olive oil in an amount from about 0.18% to about 0.3% mass per volume of the medicament, wherein said phenol comprises oleuropein; and
dimethicone.

* * * * *

UNITED STATES PATENT AND TRADEMARK OFFICE
CERTIFICATE OF CORRECTION

| | | |
|---|---|---|
| PATENT NO. | : 8,071,139 B2 | Page 1 of 1 |
| APPLICATION NO. | : 12/554364 | |
| DATED | : December 6, 2011 | |
| INVENTOR(S) | : Alan David Widgerow | |

It is certified that error appears in the above-identified patent and that said Letters Patent is hereby corrected as shown below:

At page 1 (Item 56), Col. 2, Line 5, Under "Foreign Patent Documents", please change "1997/10848" to --1997/10846--.

At column 3, Line 60, please change "macroporous" to --microporous--.

Signed and Sealed this
Second Day of October, 2012

David J. Kappos
*Director of the United States Patent and Trademark Office*